United States Patent [19]

Baskas

[11] Patent Number: 5,454,534
[45] Date of Patent: Oct. 3, 1995

[54] SURGICAL SCALPEL INSERTER DEVICE

[75] Inventor: Moris J. Baskas, Bronxvile, N.Y.

[73] Assignee: Unique Barrier Products Inc., New Rochelle, N.Y.

[21] Appl. No.: 156,683

[22] Filed: Nov. 24, 1993

[51] Int. Cl.⁶ .................................................. A47G 21/14
[52] U.S. Cl. ................ 248/37.3; 211/70.7; 248/176.1
[58] Field of Search ................. 248/176, 37.3, 248/37.6; 211/70.7; 604/192

[56] References Cited

U.S. PATENT DOCUMENTS

| | | | |
|---|---|---|---|
| 1,876,284 | 9/1932 | Fried | 211/70.7 X |
| 4,494,754 | 1/1985 | Wagner | 248/176 X |
| 4,735,617 | 4/1988 | Nelson | 604/192 |
| 4,754,943 | 7/1988 | Froutzis | 248/176 X |
| 4,830,319 | 5/1989 | Willoughby | 248/176 |
| 5,279,577 | 1/1994 | Collett | 248/176 X |
| 5,361,915 | 11/1994 | Cohen | 211/70.7 |

FOREIGN PATENT DOCUMENTS

| | | | |
|---|---|---|---|
| 438969 | 7/1991 | European Pat. Off. | 248/37.3 |
| 708992 | 8/1941 | Germany | 211/70.7 |
| 263362 | 8/1949 | Switzerland | 248/176 |
| 414975 | 6/1966 | Switzerland | 248/37.3 |

*Primary Examiner*—J. Franklin Foss

[57] ABSTRACT

A surgical scalpel blade insertion device comprises a support on which is mounted means for receiving and holding a surgical scalpel blade. Said means is configured to tightly support the blade in a vertical position with the blade part used for anchoring to a scalpel handle exposed for receiving the mating handle part. In a preferred embodiment, the blade support means comprises a spring steel U-shaped clip member mounted in a slot in the support, with the clip having a narrowed spacing located just above the support surface.

12 Claims, 4 Drawing Sheets

SURGICAL SCALPEL INSERTER DEVICE

This invention relates to a surgical scalpel inserter device to assist medical, dental, or veterinarian practitioners to mount a surgical scalpel blade on a scalpel handle while preserving blade sterilization.

BACKGROUND OF THE INVENTION

Current practices to mount scalpel blades in a sterile manner on to a conventional handle are difficult and prone to cause problems. Typically, the surgeon or his assistant will manipulate the blade package and handle while using sterile gloves. This will maintain sterility, but the person involved must hold the blade at its back while inserting it onto the handle. It can also be held by a hemostat. If care is not exercised, the sterile gloves may be cut spoiling the sterile conditions.

SUMMARY OF THE INVENTION

An object of the invention is a device for supporting the scalpel blade or scalpel package in a sterile manner if desired while attaching the handle to the blade.

In accordance with one aspect of the invention, the device comprises a support on which is mounted means for receiving and holding a surgical scalpel blade. Said means is configured to tightly support the blade in a vertical position with the blade part used for anchoring to the handle exposed for receiving the mating handle part.

In a preferred embodiment, the blade support means comprises a spring steel U-shaped clip member mounted in a slot in the support. The clip has a narrowed spacing located just above the support surface and widened spacings both above and below. This arrangement makes it very easy to insert the blade in a sterile manner within the clip so that the handle-mounting part is exposed ready for attachment to the handle.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

Figure 1:
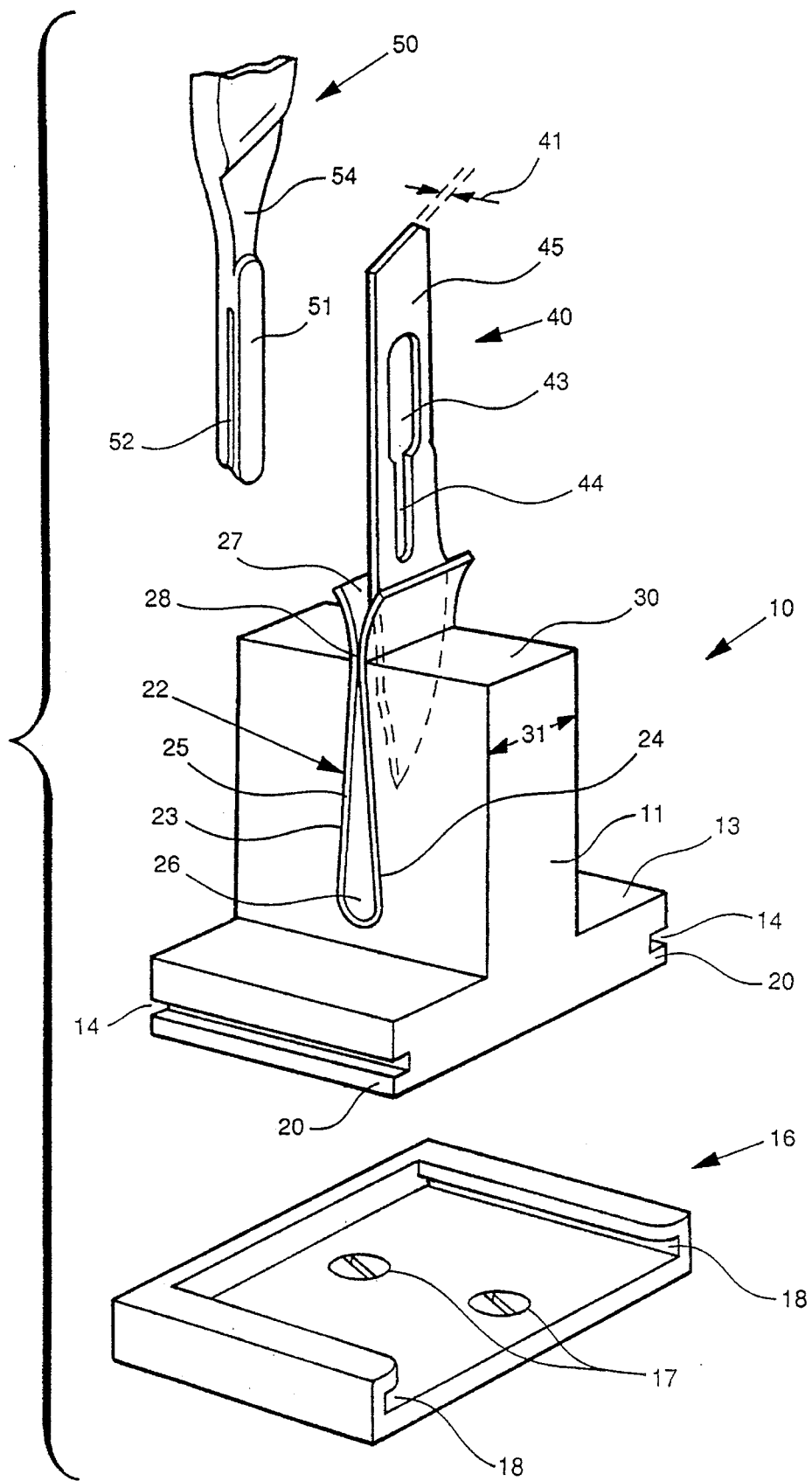
FIG. 1 is a perspective, exploded view of one form of scalpel blade insertion device according to the invention showing how the scalpel handle can be attached.

In FIG. 1, the device of the invention 10 comprises a support 11, for example, of metal or plastic in the form of a sturdy block. At the block bottom is provided a flanged portion 13 having at opposite ends a horizontal slot 14 used to anchor the support 11 to a surface of, for example, a cabinet or table (not shown). This anchoring is accomplished by way of an anchoring member 16 adapted to be screwed 17 to the table and having a recessed slot or undercut 18 sized to receive the support bottom portion 20 below the slot 14. The two can be engaged by sliding the support 11 into the member 16. The slot 18 can be slightly tapered inward so that the support 11 locks into position inside the member 16. Other forms of mounting of the support 11 to a supporting surface can be substituted. For example, the support 11 can be adhered to the base 16 by means of double-sided adhesive tape, and the base 16 can be adhered to a surface by means of double-sided tape.

The blade anchoring part of the support 11 comprises a vertically-extending slot 22 having opposed side walls 23, 24 and open sides. Mounted within the slot 22 is a spring steel clip member 25 which is generally U-shaped with widened spaced portions below 26 and above 27 a narrow-spaced portion 28 located just above the top surface 30 of the support 11, forming a generally tear-shaped member. The narrow spacing at the portion 28 is critical, and provides a friction or interference fit to the blade thickness. A conventional surgical scalpel blade 40 is shown mounted in the clip 22. The matching of the clip spacing at portion 28 is to the blade thickness indicated by reference 41. A conventional standard scalpel handle is shown at 50 with the handle part to be grasped by the user cut off. The handle anchors to the blade by means of an attachment part comprising a protruding part 51 having a groove 52 at its bottom. The protruding part 51 is configured to engage a slot having a widened part 43 in the blade and then as the handle is moved forward (downward in FIG. 1), the slot 52 engages the walls bounding the narrow slot extension 44, and as the movement contines the projection 51 snaps into place within the slot 43 with the blade upper part 45 coming to rest on a recessed area 54 at the handle end. This locks the blade 40 firmly to the handle 50. To remove the handle with the attached blade from the apparatus, the handle is simply pulled upward and out of the apparatus.

To ensure that the scalpel blade is firmly anchored to the handle, the attachment steps described above require a certain amount of force to be applied by the handle to the blade. That is the reason for the friction fit of the blade to the clip at the narrowed portion 28, which should be tight enough to keep the blade from moving during the blade-mounting procedure yet should allow the handle with the attached blade to be removed from the support 10. The widened part 27 at the top facilitates engagement of the clip by the blade. The widened part 26 at the bottom ensures that the holding pressure occurs only at the narrowed part 28 and can thus be more readily controlled. The width of the clip 25 and of the support 10, the dimension indicated by 31, is large enough to accommodate the full width of the blade 40 but is less than the width of the conventional blade package. More on this below.

Figure 3:
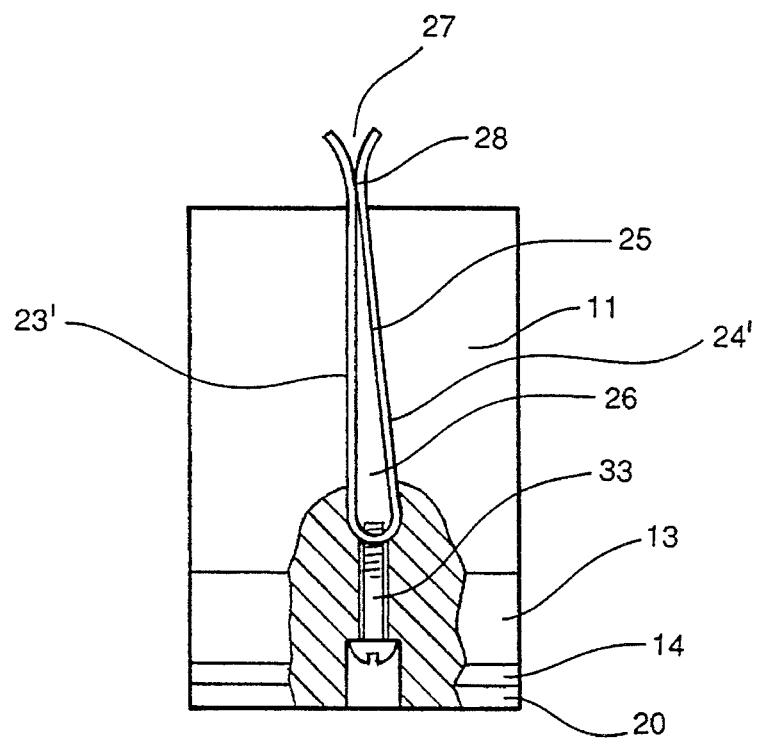
FIG. 3 is an end, partly cut-away view showing how the clip member can be attached to the support.

In operation, the sterile blade is removed from its standard sealed package and inserted in the clip member 25 on the support 10, as shown. This can be done by applying pressure to the blade while held with gloves or with a hemostat. The narrowed part 28 lies just above the surface 30 of the block so that a very small amount of play, subject to the spring pressure, exists to allow the blade to be inserted in and removed from the clip. In this embodiment, the side walls 23, 24 of the block slot 22 follow the contour of the clip sides, so no lateral give within the slot 22 exists. This shape also helps keep the clip member 25 inside the slot 22 during operation. Glue can be added if desired. In addition, if desired, the clip member 25 can be anchored in the support slot 22 by means of a screw 33 from the bottom, as shown in FIG. 3. With the blade inserted as shown in FIG. 1, the user then brings the blade handle up and inserts the projection 51 into the slot 43 and continues as described above until the blade is firmly anchored to the handle, and the latter with the attached blade can then be pulled out fron the clip member 25.

Figure 6:
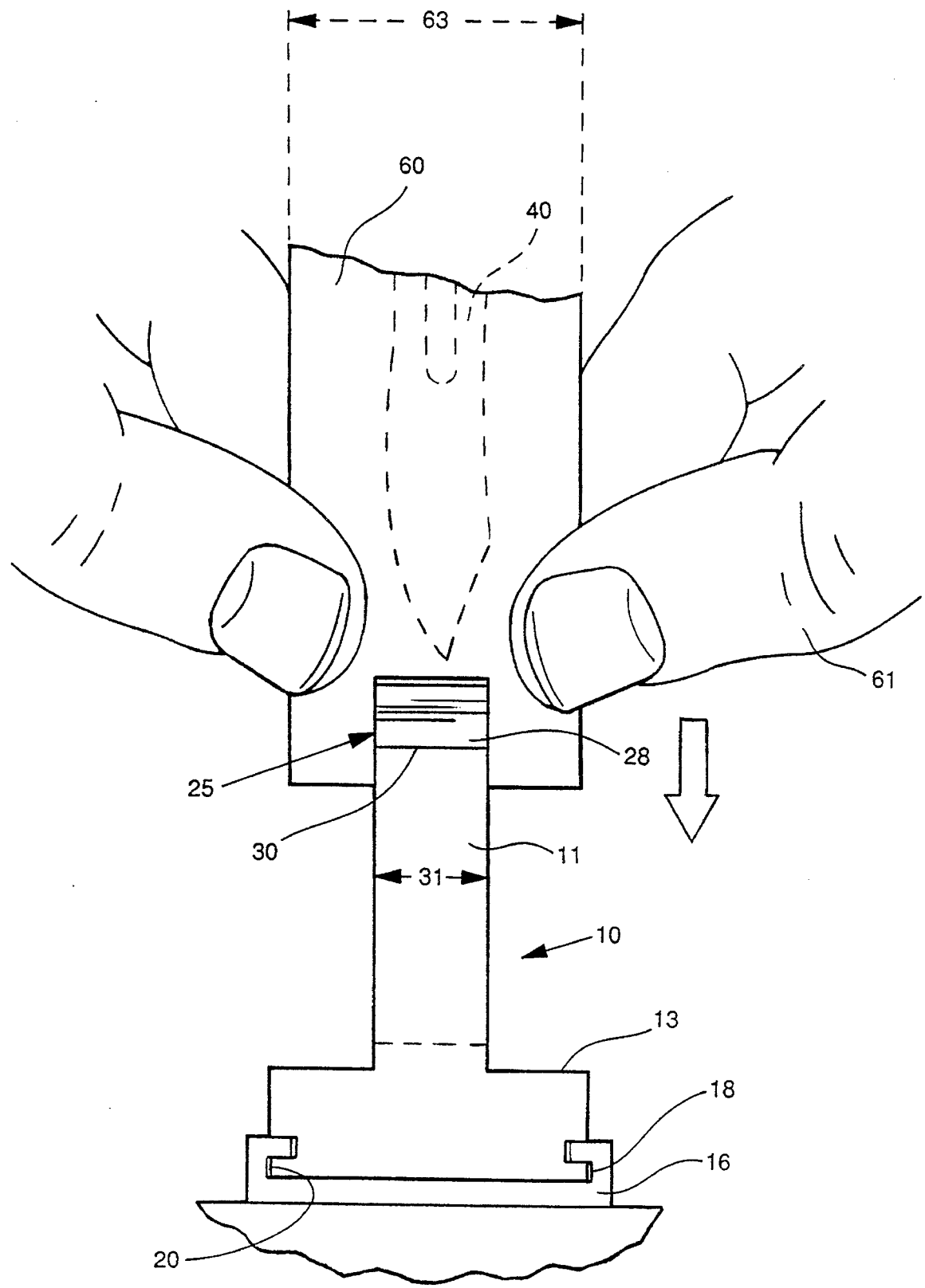
FIG. 6 shows how the blade package is mounted in the device of the invention during a handle mounting procedure.

As an alternative, as shown in FIG. 6, the blade package 60, typically sealed aluminum foil, can be inserted as shown into the clip member 25 on the support 10, by the user 61 grasping both sides of the blade package and pushing it down inside the clip narrowed portion 28 until the blade 40 is located in about the same position as in FIG. 1. The width 31 of the support 11 is sufficiently narrow relative to the width of the blade package 60, shown at 63, that the user can grasp both sides of the package while pulling down without the support block 11 interfering. When the blade 40 is in position, then the package sides 65, 66 can be peeled back without touching the blade 40 to expose the sterile blade slot 43 for attachment of the handle.

Figure 2:
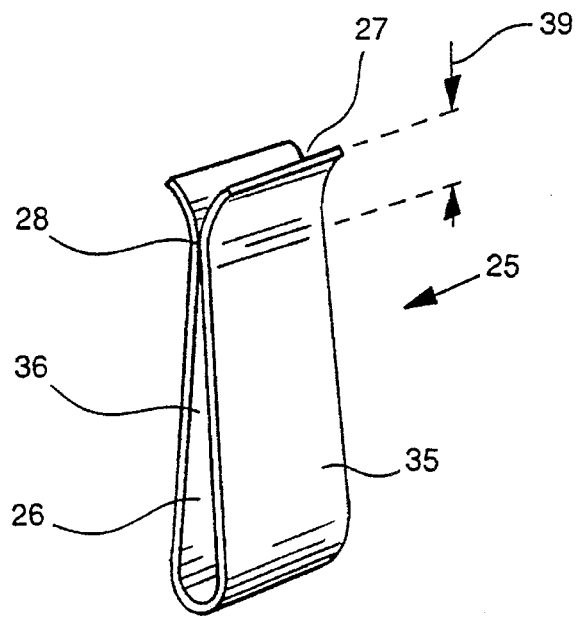
FIG. 2 is a perspective view of the clip member used in the device of FIG. 1.
Figure 4:
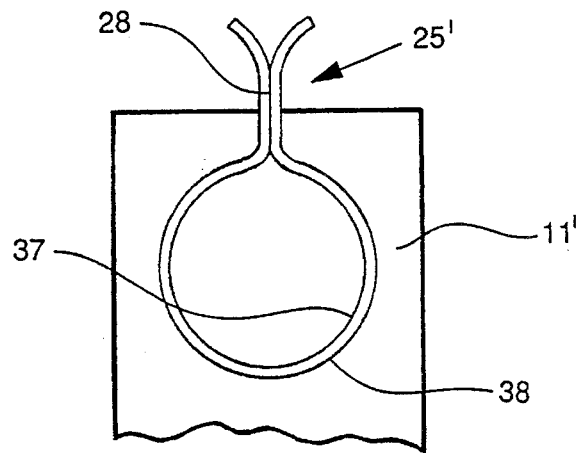
FIG. 4 is an end schematic view of another form of device according to the invention.
Figure 5:
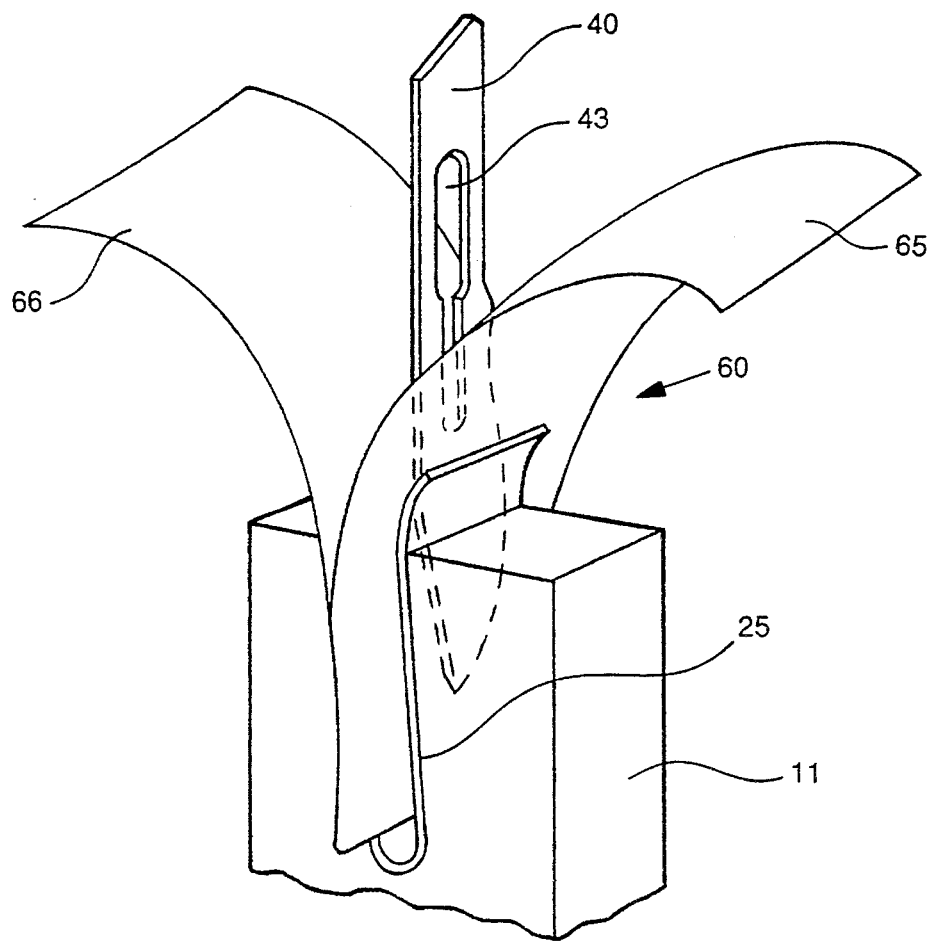
FIG. 5 is a perspective view showing how the device of FIG. 1 can be used with the blade in its sterile package.

As shown in FIG. 2, the blade side arms 35, 36 are angled equally from a center neutral axis to form the widened portion 26 and the tear drop shape, and the slot 22 in the support 11 has a similar configuration. FIG. 3 shows a modification in which one slot wall 23' is vertical, and only the other slot wall 24' is angled, with the clip 25 having a similar configuration. In the modification shown in FIG. 4, the bottom part 37 of the clip member 25' is almost circular, and the slot or opening 38 in the support body 11' has a similar shape. Again, the lower part is not as important as the narrowed part 28 of the clip member 25' which determines the holding power on the blade.

In a preferred embodiment, but not meant to be limiting, the upper part of the support body 11, above the flange 13, had a height of one inch, and a width 31 of 0.375 inch. The overall height of the clip member 25 was 1.25 inch, and the dimension indicated by reference numeral 39 was about 0.25 inch. The area of the clip side walls 35, 36 actually holding the blade tightly was about 0.125 inch high, and the critical spacing 28 was about 0.012 inch, equal to the blade thickness 41.

In place of the table mounting member 16, other means can be substituted, such as double-sided adhesive tape. The clip member can be made of spring stainless steel to provide the required pressure on the blade.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A surgical scalpel inserter device comprising:
   (a) a support having a surface containing a first opening having a defined spacing;
   (b) first means on said support for receiving and tightly holding a surgical scalpel blade within or without its sealed package, said first means comprising a clip member fitted within the first opening and having a second opening with a first narrow spacing providing a friction fit with the blade thickness;
   (c) said clip member being fitted within the first opening such that the first narrow spacing is located substantially at the support surface and is constrained laterally by the first opening defined spacing.

2. A surgical scalpel inserter device as claimed in claim 1, wherein the first means has second and third spacings each wider than the first spacing and located on opposite sides of the first spacing.

3. A surgical scalpel inserter device as claimed in claim 2, wherein said clip member comprises a generally U-shaped spring metal member.

4. A surgical scalpel inserter device as claimed in claim 3, wherein said clip member has a tear-drop shape.

5. A surgical scalpel inserter device as claimed in claim 4, wherein said second spacing forms an open end with the open end extending beyond the support surface.

6. A surgical scalpel inserter device as claimed in claim 1, wherein the clip member has a circular shape at its bottom.

7. A surgical scalpel inserter device as claimed in claim 1, wherein the support first opening comprises a slot in which the clip member is mounted, said support slot having a shape substantially matching that of the clip member.

8. A surgical scalpel inserter device as claimed in claim 3, wherein the height of the narrow spacing is about 0.125 inch, and the width of the narrow spacing is about 0.012 inch.

9. A surgical scalpel inserter device as claimed in claim 1, wherein the width of the support is sufficient to accommodate the blade thickness but is smaller than the blade sealed package width.

10. A surgical scalpel inserter device as claimed in claim 9, wherein the support width is 0.375 inch.

11. A surgical scalpel inserter device as claimed in claim 1, in combination with a surgical scalpel blade having a thickness approximately equal to the first narrow spacing and adapted to be mounted in the clip member.

12. A surgical scalpel inserter device as claimed in claim 11, further comprising a scalpel handle attached to the blade.

\* \* \* \* \*